United States Patent [19]

Leipzig

[11] 4,097,479
[45] Jun. 27, 1978

[54] SYNTHESIS OF 5-SUBSTITUTED TETRAZOLES

[75] Inventor: Theodore J. Leipzig, Elkhart, Ind.

[73] Assignee: Miles Laboratories, Inc., Elkhart, Ind.

[21] Appl. No.: 776,619

[22] Filed: Mar. 11, 1977

[51] Int. Cl.² .......................................... C07D 403/06
[52] U.S. Cl. ................................................... 544/366
[58] Field of Search ................................. 260/268 PH

[56] References Cited

U.S. PATENT DOCUMENTS

| 3,231,574 | 1/1966 | Strycker et al. | 260/268 PH |
| 3,499,900 | 3/1970 | Schut et al. | 260/308 D |

*Primary Examiner*—Jose Tovar
*Attorney, Agent, or Firm*—Myron B. Sokolowski; Richard W. Winchell

[57] ABSTRACT

Synthesis of 5-substituted tetrazoles via reaction of an organic nitrile with azide anion is improved by performing the reaction in an amine as solvent and in the presence of an acid-addition salt of the amine as catalyst.

4 Claims, No Drawings

SYNTHESIS OF 5-SUBSTITUTED TETRAZOLES

BACKGROUND

A. Field

This invention relates to the synthesis of 5-substituted tetrazoles by reacting an organic nitrile with an azide in a polar solvent, in the presence of a catalyst, and at a temperature near the boiling point of the solvent. Such synthesis is represented in the following generalized reaction equation,

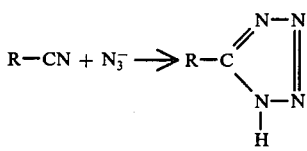

in which R is a hydrocarbon or a hetero-atom containing hydrocarbon moiety.

B. Prior Art

Finnegan et al. (J. Am. Chem. Soc., 80: 3908 [1958]; hereinafter "Finnegan") report that the synthesis of 5-substituted tetrazoles by reaction of an organic nitrile with an azide in dimethylformamide (DMF) or dimethylsulfoxide (DMSO) at a temperature near the respective boiling point of either provides higher yields than obtained by use of other solvents in that reaction. Finnegan discusses the disadvantages of using benzene, toluene, xylene, acetic acid in butanol, methyl and ethyl ethers of ethylene, ethylene glycol, methyl cellulose, and ethyl cellulose as solvents in the reaction. Such solvents require specialized glass or pressure equipment, extend reaction time, are not adaptable to large scale synthesis, and provide only modest yields. Use of either of DMF or DMSO overcomes such difficulties, increases yields, and is compatible with a variety of catalysts. Catalysts studied in the Finnegan paper in conjunction with DMF or DMSO include ammonium chloride, di(n-butyl)amine hydrochloride, aminobenzene hydrochloride, ethane sulfonic acid, boron trifluoride in diethyl ether, tetramethylammonium chloride, and lithium chloride. While DMF and DMSO overcome the difficulties of other solvents in the synthesis of 5-substituted tetrazoles, one still encounters ". . . sublimation of ammonium azide to the cooler portions of the reaction flask and the condenser." (Finnegan, p. 3909).

U.S. Pat. No. 3,231,574 (1/66; "Strycker") and U.S. Pat. No. 3,499,900 (3/70; "Schut") collectively teach a method for the synthesis of pharmacologically active 5-substituted tetrazoles characterized by the formula,

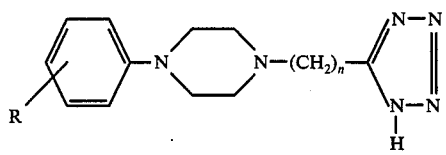

in which R is a hydrogen atom, a halogeno, or a trifluoromethyl substituent and n is an integer of the set 1-4. That method involves the reaction of an appropriate nitrile of the general formula,

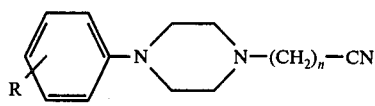

(R and n having the same meaning as defined above), with an alkali-metal or ammonium azide in a suitable solvent, in the presence of a catalyst, and at a temperature nearing the boiling point of the solvent. While Strycker alleges that ". . . any organic solvent which will facilitate the reaction, that is, any ionizing solvent in which the reactants are soluble . . ." can be used in the method, the patent teaches DMF is preferred (column 1, lines 54–58). The reactions disclosed in the examples of Strycker utilize DMF only. With respect to catalysts used in the method, the patent explains that Lewis-acid catalysts can be used but that ammonium hydrochloride or an amine hydrochloride are preferred. Time of the reaction, according to Strycker, ranges between 10 and 24 hours. Schut contains a similar, if not verbatim, teaching (column 2, lines 9–24).

The following references are representative of the level of skill in the relevant field: (1) Lieber et al., J. Org. Chem., 22: 238 [1957]); (2) Mikina and Herbst, ibid: 1082 [1957]; (3) Herbst and Wilson, ibid.: 1142 [1957]; (4) Behringer and Kohl, Ber., 89: 2648 [1956]; (5) Holland and Pereia, J. Med. Chem., 10: 149 [1967]; (6) Adelstein, J. Med. Chem. 16: 309 [1973].

Collectively the prior art demonstrates the advantages of DMF and DMSO as solvents in the synthesis of a 5-substituted tetrazole from a corresponding nitrile and an azide. None of the prior art references discloses or suggests the combined use of an amine as solvent and an acid-addition salt of the amine as catalyst in such synthesis.

DETAILED DESCRIPTION OF THE INVENTION

The preceding summary of the field and prior art relating to this invention discusses a known method for preparing 5-substituted tetrazoles involving the reaction of a hydrocarbon or a hetero-atom containing hydrocarbon with an azide in a polar solvent, in the presence of a catalyst, and at a temperature near the boiling point of the solvent. This invention is an improvement of such method, which improvement resides in the combined use of an amine as the solvent and an acid-addition salt of the amine as the catalyst. The improvement of the method increases the yield of the 5-substituted tetrazole, decreases reaction time, and eliminates operational difficulties associated with the method.

The improvement has applicability in a method for the preparation of 5-substituted tetrazoles in a general reaction of the type,

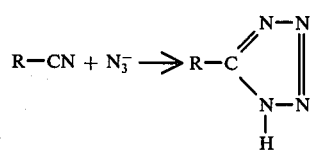

wherein R is a hydrocarbon or a hetero-atom containing hydrocarbon moiety, as well as in a method for the preparation of certain 5-[ω-(4-substituted-1-piperazyl]-tetrazoles,

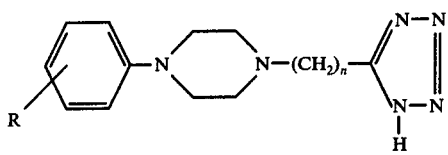

by the reaction of a 4-substituted-1-(ω-cyanoalkyl)piperazine,

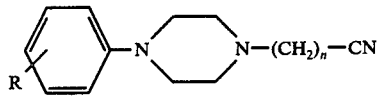

with an ammonium or alkali-metal azide. In I and II, R is a hydrogen atom, a halogeno, or a trifluoromethyl substituent and n is an integer of the set 1–4. In particular the improvement has preferred applicability in the preparation of 5-[2-(4-phenyl-1-piperazyl)ethyl]tetrazole by the reaction of 4-phenyl-1-(2-cyanoethyl)piperazine with an ammonium or alkali-metal azide.

As mentioned earlier, the essential feature of this invention is the use of a solvent-catalyst system comprising an amine as the solvent and an acid-addition salt of the amine as the catalyst in the prior art method. All operational parameters of the latter, except time of reaction, remain the same, e.g. heating the reaction mixture near the boiling point of the solvent.

The amines used in the solvent-catalyst system in the improved method have a $pK_b$ in the range of 2–6 and a boiling point of from about 100° to 250° C. Representative of such amines, but not exhaustively so, are: pyrrole, 1,2-isopyrrole, 1,3-isopyrrole, pyrazole, 1,2,3-triazole, 1,2,4-triazole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,4-dioxazole, 1,3,4-dioxazole, pyridine, pyridazine, pyramidine, pyrazine, piperazine, 1,3,5-triazine, 1,2,4-triazine, 1,2,3,-triazine, 1,2,4-oxazine, 1,3,2-oxazine, 1,3,6-oxazine, 1,4-oxazine, 1,4-isoxazine, o-isoxazine, p-isoxazine, morpholine, azepine, 1,2,4-diazepine, monoalkylamines containing 2 to 4 carbon atoms, and dialkylamines having from 2–8 carbon atoms.

The acid addition salts of the amine used in the solvent-catalyst system in the improved method include, but are not limited to those obtained with inorganic or organic acids such as: hydrochloric, hydrobromic, hydroiodic, sulfuric, nitric, phosphoric, formic, acetic, propionic, pivalic, diethylacetic, oxalic, malonic, succinic, pimelic, fumaric maleic, lactic, tartaric, sulfamic, benzoic, salicylic, phenylpropionic, citric, gluconic, ascorbic, isonicotinic, sulfonic, ethanesulfonic, or p-toluenesulfonic acid.

The stoichiometric amount of the acid-addition salt to the nitrile is not critical; a ratio of 1:1, however, is preferred.

Reaction from the improved method is from 2 to 6 hours.

The use of an amine as solvent and of its acid-addition salt as catalyst in the prior art method of preparing 5-substituted tetrazoles increases the yields of the latter by 100 to 200% for the same reaction time, allows the reaction to proceed in an open vessel, and thus eliminates the hazard of sublimation of ammonium azide on the reaction vessel or condenser. Succeeding examples 1 and 2 demonstrate that the discovered improvement permits dramatic increases in yield, as summarized by the following table.

TABLE A

Yields of 5-[2-(4-Phenyl-1-Piperazyl)Ethyl)Tetrazole (I: R=H; n=z) Obtained from the Reaction of 4-Phenyl-1-(2-Cyanoethyl) Piperazine (II: R=H; n=z) Using Prior Art Solvent-Catalyst Systems and the Amine/Aminol Acid-Addition Salt System

| Ex. | Solvent | Catalyst | Yield | Ratio of Yield Obtained in Ex. 1 to That in Ex. 2 |
|---|---|---|---|---|
| 1 | Morpholine | Morpholine . HCl | 60% | — |
| 2 | DMF | NH₄Cl | 15% | 4 |
| 2 | DMF | Morpholine . HCl | 31% | 2 |

DESCRIPTION OF THE PREFERRED EMBODIMENTS

EXAMPLE 1

IMPROVED SYNTHESIS OF 5-[2-(4-PHENYL-1-PIPERAZYL)ETHYL]-TETRAZOLE

Sodium azide (65 g; 1.0 mol), 4-phenyl-1-(2-cyanoethyl)-piperazine (215 g; 1.0 mol), and morpholine hydrochloride (124 g; 1.0 mol) were dissolved in 1 liter of morpholine, and heated at 120°–125° C with stirring for 4 hours. After the reaction mixture was allowed to cool to room temperature, it was filtered, and the solvent was removed in vacuo. The residue was mixed in water, and the pH of the resulting solution was adjusted to 5. Crude 5-[(4-phenyl-1-piperazyl)ethyl]tetrazole was collected by filtration and was dried; yield — 170 g. The crude product was recrystallized from water and dried; yield — 155 g (60% yield; m.p. 190°–194° C).

Analysis:

Calculated for $C_{13}H_{18}N_6$: C, 60.46; H, 6.97; N, 32.56
Found: C, 60.35; H, 6.81; N, 32.87.

EXAMPLE 2

COMPARATIVE RESULTS OBTAINED RESPECTIVELY USING AMMONIUM CHLORIDE AND MORPHOLINE HYDROCHLORIDE AS CATALYSTS AND DIMETHYLFORMAMIDE (DMF) AS THE SOLVENT

A. AMMONIUM CHLORIDE AS CATALYST IN DMF.

Sodium azide (65 g; 1 mol), ammonium chloride (53.5 g; 1.0 mol), and 4-phenyl-1-(2-cyanoethyl)piperazine (2.15 g; 1.0 mol) were dissolved in 300 ml of DMF and then heated at 120°–125° C for 5.5 hours. After cooling the mixture and removing the inorganic salts by filtration, the filtrate was stripped off in a water bath in vacuo. The residue was slurried in ether, and the ether solution was decanted to remove starting material. The residue then was slurried in acetone and cooled in an ice bath. Crude product was collected by filtration, dried, and recrystallized from water with the aid of activated charcoal. Yield of recrystallized product was 38 g (15% yield). Melting point of recrystallized product was 190°–194° C.

B. MORPHOLINE HYDROCHLORIDE AS CATALYST IN DMF

Sodium azide (16.5 g; 0.25 mol), morpholine hydrochloride (31 g; 0.25 mol), and 4-phenyl-1-(2-cyanoethyl)-piperazine (54 g; 0.25 mol) were dissolved in 250 ml of DMF and then heated at 125° C for 5.5 hours. The product was worked up as in Example 2A. Yield of recrystallized product was 20 g (31% yield). Melting point of the recrystallized product, 188°–192° C.

What is claimed is:

1. In a method for the preparation of tetrazolyl compounds having the formula,

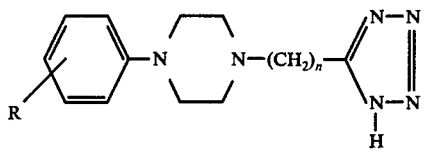

wherein and elsewhere in this claim R is a hydrogen atom, a halogeno, or a trifluoromethyl substituent and $n$ is an integer of the set 1–4, by reacting a nitrile of the formula,

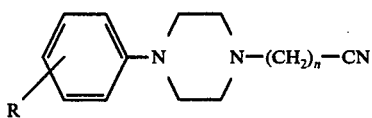

with an alkali-metal or ammonium azide in a polar organic solvent, in the presence of a catalyst, and at a temperature near to the boiling point of the solvent, the improvement comprising:

reacting the nitrile and the azide in an amine having a $pK_b$ of from 2 to 6 and a boiling point of from 100° to 250° C as the solvent and in the presence of an acid-addition salt of the amine as the catalyst.

2. In a method for the preparation of tetrazolyl compounds having the formula,

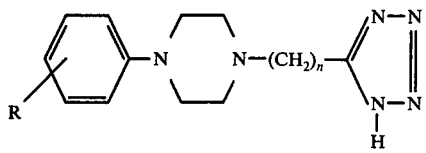

wherein and elsewhere in this claim R is a hydrogen atom, a halogeno, or a trifluoromethyl substituent and $n$ is an integer of the set 1–4, by reacting a nitrile of the formula,

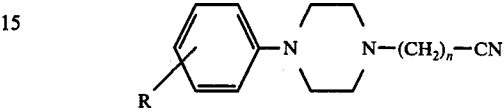

with an alkali-metal or ammonium azide in a polar organic solvent, in the presence of a catalyst, and at a temperature near to the boiling point of the solvent, the improvement comprising:

reacting the nitrile and the azide in morpholine as the solvent and in the presence of morpholine hydrochloride as the catalyst.

3. In a method for the preparation of 5-[2-(4-phenyl-1-piperazyl)ethyl]tetrazole by reacting 4-phenyl-1-(2-cyanoethyl)piperazine with an alkali-metal or ammonium azide in a polar solvent in the presence of a catalyst, and at a temperature near the boiling point of the solvent, the improvement comprising:

reacting the 4-phenyl-1(2-cyanoethyl)piperazine and the azide in an amine having a $pK_b$ of from 2 to 6 and a boiling point of from 100° to 250° C as the solvent and in the presence of an acid-addition salt of the amine as the catalyst.

4. In a method for the preparation of 5-[2-(4-phenyl-1-piperazyl)ethyl]tetrazole by reacting 4-phenyl-1-(2-cyanoethyl)piperazine with an alkali-metal or ammonium azide in a polar solvent in the presence of a catalyst, and at a temperature near the boiling point of the solvent, the improvement comprising:

reacting the 4-phenyl-1(2-cyanoethyl)piperazine and the azide in morpholine as the solvent and in the pressence of morpholine hydrochloride as the catalyst.

* * * * *